United States Patent [19]

Chance et al.

[11] Patent Number: 5,386,827
[45] Date of Patent: Feb. 7, 1995

[54] QUANTITATIVE AND QUALITATIVE IN VIVO TISSUE EXAMINATION USING TIME RESOLVED SPECTROSCOPY

[75] Inventors: Britton Chance, Marathon, Fla.; Kenneth J. Kaufmann, New Providence, N.J.

[73] Assignee: NIM Incorporated, Philadelphia, Pa.

[21] Appl. No.: 40,168

[22] Filed: Mar. 30, 1993

[51] Int. Cl.$^6$ .............................................. A61B 6/00
[52] U.S. Cl. .................................. 128/633; 128/664; 128/665
[58] Field of Search .................. 128/633, 664, 665; 356/39–41; 250/339, 341

[56] References Cited

U.S. PATENT DOCUMENTS

| | | | |
|---|---|---|---|
| 4,223,680 | 9/1980 | Jobsis | 128/633 |
| 4,281,645 | 8/1981 | Jobsis | 128/633 |
| 4,321,930 | 3/1982 | Jobsis et al. | 128/633 |
| 4,556,057 | 12/1985 | Hiruma et al. | 128/303.1 |
| 4,592,361 | 6/1986 | Parker et al. | 128/633 |
| 4,675,529 | 6/1987 | Kushida | 250/458.1 |
| 4,832,035 | 5/1989 | Cho et al. | 128/633 |
| 4,895,156 | 1/1990 | Schulze | 128/665 |
| 4,972,331 | 11/1990 | Chance | 364/550 |
| 5,090,415 | 2/1992 | Yamashita et al. | 128/665 |
| 5,119,815 | 9/1992 | Chance | 128/633 |
| 5,187,672 | 2/1993 | Chance et al. | 364/550 |

OTHER PUBLICATIONS

Bonner et al., "Model for photon migration in turbid biological media", *J. Opt. Soc. Am. A.* 4:423–432 (1987).
Chance et al., "Comparison of time-resolved and -unresolved measurements of deoxyhemoglobin in brain", *Proc. Natl. Acad. Sci. USA* 85:4971–4975 (1988).
Chance, "Phosphorylation Efficiency of the Intact Cell", *J. Biol. Chem.* 234:3036–3040 (1959).
Chance, "Rapid and Sensitive Spectrophotometry. I. The Accelerated and Stopped-Flow Methods for the Measurement of the Reaction Kinetics and Spectra of Unstable-Compounds, et al.", *J. Biol. Chem.* 179:619–639 (1949).
Chance, "Spectrophotometry of Intracellular Respiratory Pigments", *Science* 120:767–775 (1954).
Chance, "Time-Resolved Spectroscopy of Hemoglobin and Myoglobin in Resting and Ischemic Muscle", *Analytical Biochemistry* 174:698–707 (1988).
Jobsis et al., "Reflectance spectrophotometry of cytochrome aa$_3$ in vivo", *J. Applied Physiology: Respiratory Environmental and Exercise Physiology* 43:858–872 (1977).
Lakowicz, "Gigahertz Frequency-Domain Fluorometry: Resolution of Complex Intensity Decays, Picosecond Processes and Future Developments", *Photon Migration in Tissues*, pp. 169–186 (1989).
Rosenthal et al., "Effects of Respiratory Gases on Cytochrome A in Intact Cerebral Cortex: Is There A Critical Po$_2$?", *Brain Research* 108:143–154 (1976).
Tamura et al., "Simultaneous Measurements of Tissue Oxygen Concentration and Energy State by Near-Infrared and Magnetic Resonance Spectroscopy", *Oxford Press*, pp. 159–163 (1989).

*Primary Examiner*—Ruth S. Smith
*Attorney, Agent, or Firm*—Fish & Richardson

[57] ABSTRACT

A system for examination of biological tissue of a subject includes a light source, a light detector, a gated integrator and a integrator timing control adapted to integrate detected photons over at least two selected time intervals. The light source is adapted to introduce into the tissue, at an optical input port, pulses of electromagnetic radiation of a selected wavelength in the visible or infra-red range having duration on the order of a nanosecond or less. The detector detects, at an optical detection port, photons of modified pulses that have migrated in the tissue from the input port. The integrator and the integrator timing control register all photons arriving at the detector port over preselected time intervals of the arrival time of the modified pulses. The time-dependent shape of the modified pulses reflects the scattering and absorptive properties of the examined tissue. A processor adapted to receive data from the integrator determines a physiological property of the examined tissue based on the number of photons integrated over each time interval.

30 Claims, 9 Drawing Sheets

QUANTITATIVE AND QUALITATIVE IN VIVO TISSUE EXAMINATION USING TIME RESOLVED SPECTROSCOPY

CROSS-REFERENCE TO RELATED APPLICATIONS

The present invention is related to U.S. patent application Ser. No. 07/876,364 filed Apr. 30, 1992, which is a continuation application of U.S. Pat. No. 5,119,815, issued Jun. 9, 1992, both of which are incorporated by reference as if set forth in their entireties herein.

BACKGROUND OF THE INVENTION

The present invention relates to a time resolved spectroscopy method and apparatus for in vivo characterization of tissue.

Continuous wave (CW) tissue oximeters have been widely used to determine in vivo concentration of an optically absorbing pigment (e.g., hemoglobin, oxyhemoglobin) in biological tissue. The CW oximeters measure attenuation of continuous light in the tissue and evaluate the concentration based on the Beer Lambert equation or modified Beer Lambert absorbance equation. The Beer Lambert equation (1) describes the relationship between the concentration of an absorbent constituent (C), the extinction coefficient ($\epsilon$), the photon migration pathlength $<L>$, and the attenuated light intensity ($I/I_o$).

$$\frac{\log[I/I_0]}{<L>} = \Sigma \epsilon_i C_i \quad (1)$$

The CW spectrophotometric techniques cannot determine $\epsilon$, C, and $<L>$ at the same time. If one could assume that the photon pathlength were constant and uniform throughout all subjects, direct quantification of the constituent concentration (C) using CW oximeters would be possible.

In tissue, the optical migration pathlength varies with the size, structure, and physiology of the internal tissue examined by the CW oximeters. For example, in the brain, the gray and white matter and the structures thereof are different in various individuals. In addition, the photon migration pathlength itself is a function of the relative concentration of absorbing constituents. As a result, the pathlength through an organ with high blood hemoglobin concentration, for example, will be different from the same with a low blood hemoglobin concentration. Furthermore, the pathlength is frequently dependent upon the wavelength of the light since the absorption coefficient of many tissue constituents is wavelength dependent. Thus, where possible, it is advantageous to measure directly the pathlength when quantifying the hemoglobin concentration in tissue.

Frequently, it is advantageous to determine the hemoglobin saturation in vivo. Although the arterial oxygen saturation in a perfused organ can be quantified, it is not possible to estimate the change in the hemoglobin oxygen concentration as it leaves an artery and enters the capillary bed; nor is it possible to determine the intermediate value of oxygen saturation in a particular capillary bed from the venous drainage since no technique has been devised for drawing a blood sample directly from the capillary bed.

In contrast to CW oximeters, time resolved spectroscopy (TRS-pulse) can measure directly the average pathlength of migrating photons as well as other tissue properties such as the absorption and scattering of light in tissue.

As described in the above-cited patent and patent applications, the TRS system irradiates tissue with pulses of light of $10^{-10}$ sec. duration that migrate through a path between an optical input port and an optical detection port. The shape of the input pulse is modified by the scattering and absorption properties of the tissue. The modified light is detected by a photomultiplier, amplified and stored in a multichannel analyzer. The multichannel analyzer collects only a single photon for each input light pulse. A signal from each detected photon is encoded for time delay and recorded. The pulses are accumulated over a relatively long time interval (on the order of 5 minutes) so that approximately $10^5$ counts are collected at the detected pulse maximum. The relatively long counting time is required to obtain reasonable statistics so that a reasonable fit over three or four decades of the logarithmic slope on the detected pulse can be obtained.

For some applications, the relatively long collection time is a disadvantage. Furthermore, the instrumentation of the single photon counting TRS-pulse system is costly when compared with the CW systems. The relative complexity, cost, and size of the TRS-pulse system, of the embodiment illustrated in U.S. Pat. No. 5,119,815, could present some barriers to marketing for certain applications in today's cost-conscious health care industry.

Thus, there is a need for a cost-effective time resolved spectroscopic system that requires a relatively short period of data accumulation for quantitative and qualitative tissue examination.

SUMMARY OF THE INVENTION

In one aspect, the invention features a method and a system for examination of biological tissue of a subject using a light source, an optical detector, a gated integrator with an integrator timing control and a processor. The scattering and absorptive properties of the examined tissue are determined by photons migrating between an optical input port connected to the source and an optical detection port connected to the detector. The light source is adapted to introduce into the tissue, at the input port, pulses of electromagnetic radiation of a selected wavelength in the visible or infra-red range, the pulses having duration on the order of a nanosecond or less. The detector is adapted to detect, at the detection port, photons of modified pulses that have migrated in the tissue from the input port. The gated integrator and the integrator timing control are adapted to integrate the photons over at least two selected time intervals separately spaced over the arrival time of the modified pulses. The processor is adapted to determine a physiological property of the examined tissue based on the number of photons integrated over each time interval.

Preferred embodiments of this aspect of the invention may include one or more of the following features.

The system further includes an additional gated integrator and integrator timing control adapted to integrate the photons over a selected time interval spaced over the arrival time of the modified pulses.

The processor can determine the absorption coefficient ($\mu_a$) of the examined tissue based on the number of photons integrated over at least two selected time intervals separately spaced over the arrival time of the modified pulses.

The absorption coefficient is determined from the decay slope of the arrival time of the modified pulses.

The gated integrator, the integrator timing control and the processor are adapted to determine the delay time ($t_{max}$) between the introduced pulse and a time at which the detected profile of the corresponding modified pulse a maximum value.

The processor is further adapted to determine the effective scattering coefficient $(1-g)\cdot\mu_s$ of the examined tissue using the formula:

$$(1 - g)\mu_s = \frac{1}{\rho^2} (4\mu_a c^2 t_{max}^2 + 10ct_{max}) - \mu_a$$

wherein $\rho$ is a distance between the input and detection ports and c is speed of light in the medium.

The light source is further adapted to introduce into the tissue, at the input port, the pulses of electromagnetic radiation of a second selected wavelength in the visible or infra-red range, and the detector is further adapted to detect, at the detection port, photons of modified pulses of the second wavelength that have migrated in the tissue from the input port. The gated integrator and the integrator timing control are further adapted to integrate the detected photons over at least two selected time intervals separately spaced over the arrival time of the modified pulses. The processor is further adapted to determine a physiological property of the examined tissue based on the number of photons integrated over each time interval for each selected wavelength.

The absorption coefficient ($\mu_a$) of the examined tissue can be determined by the processor based on the number of photons integrated over at least two selected time intervals separately spaced over the arrival time of the modified pulses.

The processor is further adapted to determine concentration of a tissue pigment based on the absorption coefficients at each selected wavelength.

The processor is further adapted to determine the oxygen saturation Y based on the ratio of the absorption coefficients at two selected wavelengths.

The gated integrator and the integrator timing control are further adapted to integrate the detected photons over several selected time intervals separately spaced over the entire arrival time of the modified pulses, and the processor is further adapted to determine intensity profile of the modified pulses over the entire arrival time.

The processor is further adapted to determine a mean pathlength of the distribution of the photon migration pathlengths.

The determined pathlength is used to calibrate data measured by a continuous wave oximeter.

The light source includes a laser driven by a pulse generator and a pulser. The wavelength of the source is in the range of 600 nm to 1000 nm.

DESCRIPTION OF THE PREFERRED EMBODIMENT

Figure 1:
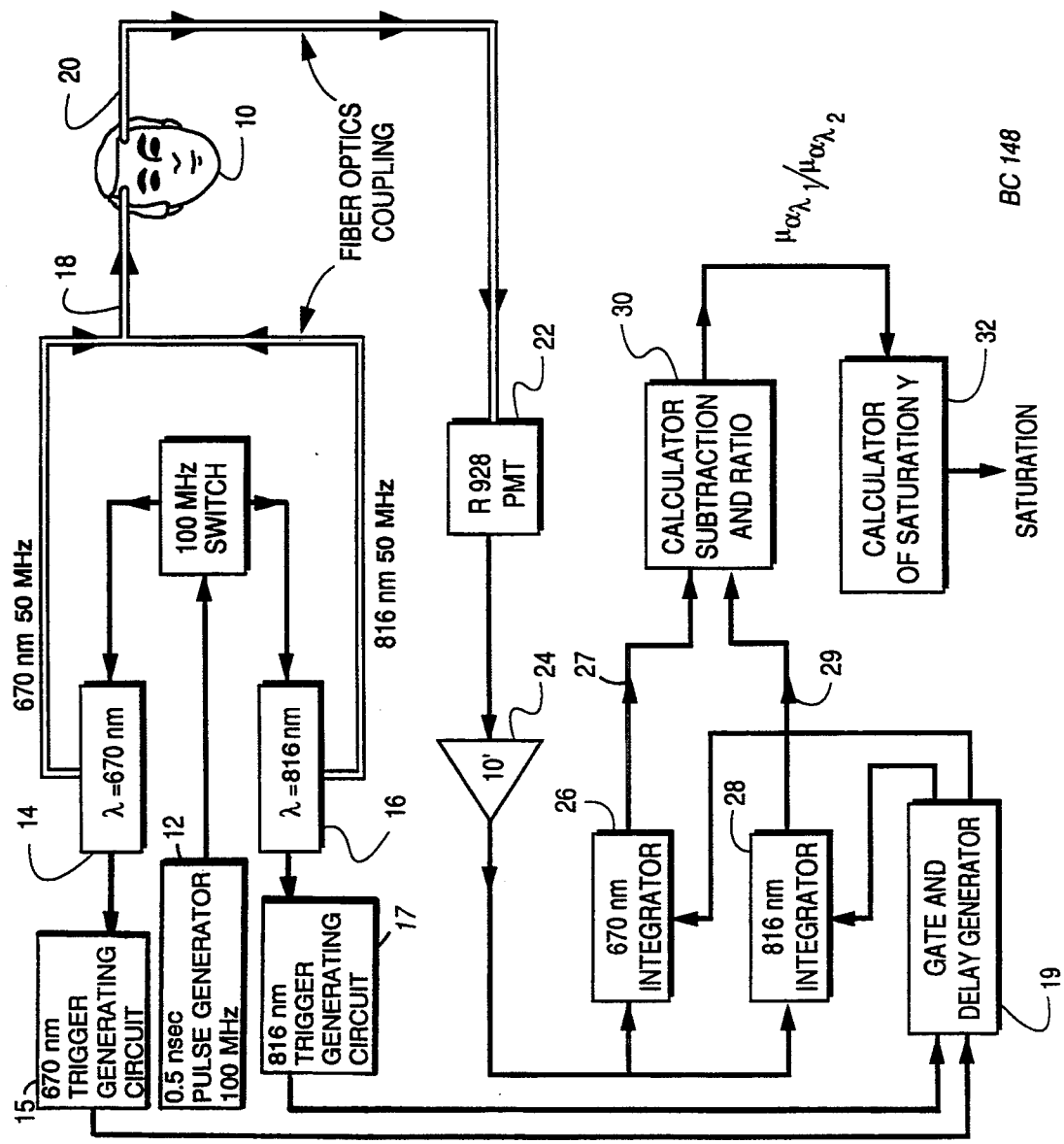
FIG. 1 is a block diagram of a two gate integrator TRS-pulse system in accordance with one embodiment of the present invention.
Figure 2:
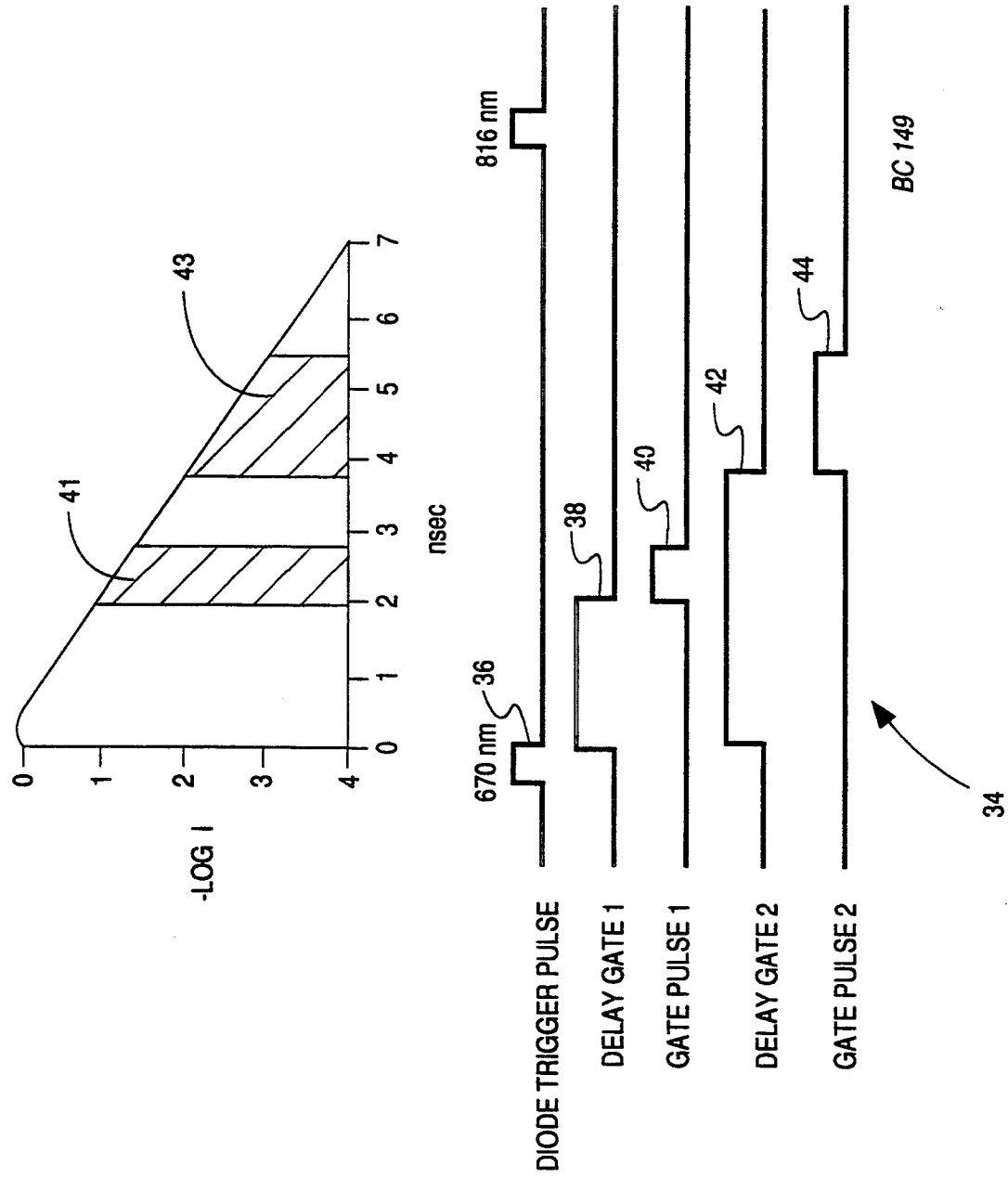
FIG. 2 is a timing diagram of the system of FIG. 1.

As described in Disclosure Document No. 301,998, entitled Simplified TRS filed with The Patent and Trademark Office on Feb. 12, 1992, FIG. 1 (BC148 of the disclosure document) illustrates the appropriate electronic components, consisting of a 0.5 nanosecond pulse generator (12) operating at 100 MHz and a pulse train at 100 MHz with a duration of 0.5 nanosecond. These pulses are alternately switched to the 670 nm laser diode (14) or to the 816 nm laser diode (16) to illuminate the subject (10), for example the forehead, at a frequency of 50 MHz. The output (20) is detected by an R928 PMT (22) connected to a wide band amplifier/impedance changer (24) and then to the two parallel pulse integrators (26 and 28). These pulse integrators are activated at the times corresponding to the illumination of the subject by the two wavelengths (670 and 816 nm). The trigger generator for this follows the timing diagram (FIG. 2) and consists of two trigger generating circuits (15, 17), each triggered by a diode pick up from the corresponding light source. Thus the integrators (26 and 28) are activated only when the particular light source is activated. Their outputs (27 and 29) are connected to the subtraction and ratio circuit (30), so that the output is the ratio of the two wavelengths, which, in turn, is connected to a simple computer (32) for saturation.

The gate and delay generator (19) operates in accordance with the timing diagram (FIG. 2) and consists of two generators, each separately triggered by the appropriate trigger pulse (alternatively, the same gate-generating components can be time shared with electronic switches).

A trigger pulse (36) obtained from the 670 nm light source sets off the timing diagram (34) to afford a delay gate (38) for gate pulse 1 (40), which is from 2-2.7 nanoseconds. The gate triggers a pulse integrating circuit (26) which integrates detected photons (41). The same is done for the 816 nm light source wherein the gate (19) triggers the second pulse integrating circuit (28). Subsequently, the delay time of delay gate 2 is chosen so that delay gate 2 (42) triggers gate pulse 2 (44) from 3.8–5.4 nanoseconds for pulses from the two light sources as described above or shown in FIG. 2.

An analog voltage is then available which represents this integral, which is then converted into logarithms with an analog (or digital) circuit. The result of these logarithms, divided by the known time difference between the two, gives, with proper scaling, $\mu_a$ for the particular wavelength—for example, 670 nm. Another wavelength is available, namely 816 nm, so that the $\mu_a$ values of the two wavelengths can be obtained and entered into the usual calculation for saturation (32).

Figure 3:
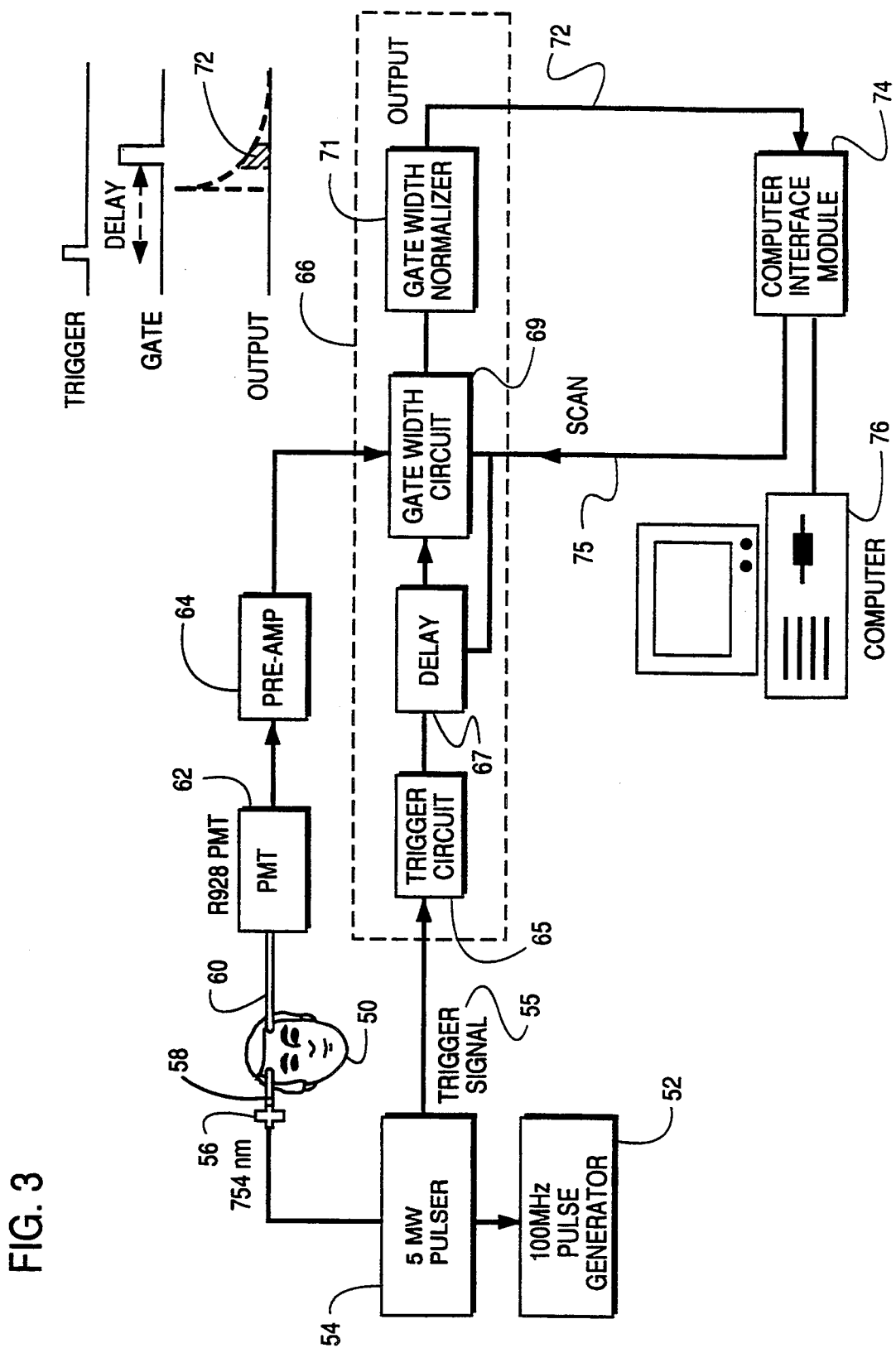
FIG. 3 is a block diagram of a single integrator single wavelength TRS-pulse system in accordance with another embodiment of the present invention.

FIG. 3 shows diagrammatically another implementation of the "boxcar" simplified TRS system that uses a single integrator for the gated photon signal integration. A pulse generator 52 operating at a frequency on the order of 100 MHz connected to a pulser 54 drives a laser 56 (e.g., Hamamatsu PLP-10 pulsed laser diode). Laser 56 generates a train of light pulses of a selected wavelength (e.g., 754 nm) and constant duration on the order of 100 psec (Pulses of the order of a nanosecond can also be used). The light pulses are coupled to an optical fiber 58 and are introduced to subject 50 at an input port. Transmitted photons migrate in the subject and arrive at a detection port of an optical fiber 60. In the migration process, the input pulse has been modified by the scattering and absorptive properties of tissue of subject 50. Photons arriving at the detection port are transmitted to a detector 62, (for example, Hamamatsu photomultipliers R928, R1517, MCP R1712, R1892 or other).

The output of detector 62 is amplified in a wide band preamplifier/impedance changer 64 and coupled to a boxcar integrator 66. Integrator 66 activated by a pulse gate collects all arriving photons over a predetermined time interval. The integrator output (72) is sent to computer interface module 74. Computer 76 stores the total number of counts detected during the collection interval of integrator 66.

Integrator 66 includes a trigger 65 that is triggered by a signal 55 from pulser 54. Trigger 65 activates a delay gate 67 that, in turn, starts counting of all detected photons during the time interval specified by a gate width circuit 69. Output from a gate width normalizer 71 is an analog signal or a digital signal representing all photons that arrived at the detection port during the preselected gate width interval. A suitable integrator can be achieved by using SR 250 manufactured by Stanford Research Systems.

Depending on the application, computer 76 sets the delay time of delay gate 67 and the gate width time of gate width circuit 69. The system can scan integration gate widths over the whole time profile of the detected pulse. Gate width normalizer 71 adjusts the width of the integration time depending on the detected signal level. The gate width may be increased logarithmically for smaller signals in accordance with the exponential decay of the fall of the detected pulse; this increases the signal to noise ratio. The system operates at a repetition rate of at least 10 KHz.

Figure 4:
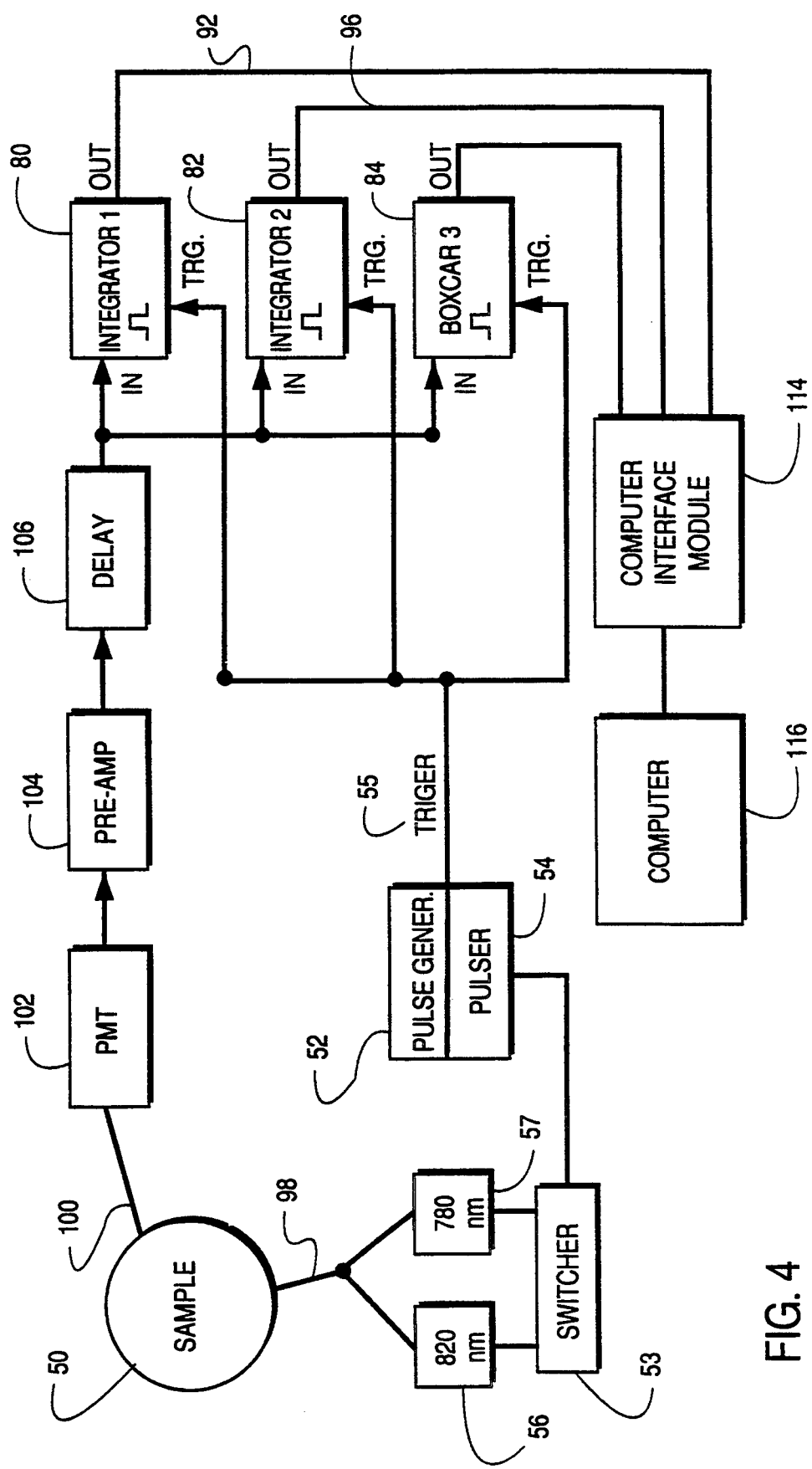
FIG. 4 is a block diagram of a multiple gate integrator TRS pulse system in accordance with another embodiment of the present invention.

Referring to FIG. 4, alternatively, multiple (at least three), parallel integrators are used in a faster and more efficient system. This system, same as the system of FIG. 3, may be used to determine the whole profile of the detected pulse (89) shown in FIG. 5, by appropriately selecting the delay gates and the gate widths.

Pulse generator 52 connected to a pulser 54 drive alternately laser 56 and 57. The alternate coupling is provided by a switcher 53 that operates at frequencies on the order of $10^7$ Hz. Pulses of light of wavelength in the visible or infra-red range and duration $10^{-9}$ to $10^{-10}$ second are alternately coupled to subject 10 via optical fibers 98 or other light guide. The light pulses are modified by tissue of subject 50 positioned between the input port of fiber 98 and the detection port of fiber 100. The modified pulses are detected by detector 102 and the detected signal is amplified by preamplifier 104. Integrators 80, 82, and 84 collect data during selected gate width intervals, as shown on the timing diagram of FIG. 5A. Trigger 55 correlated with the input pulse, triggers delay gates 1, 2, and 3 (shown in FIG. 5A) that are set to have selected delay times. Each delay gate then triggers its corresponding integrator that collects all photons that arrive at the detector during the delay width time. Each integrator collects photons arriving at the detection port during its integration time defined by the gate width. This configuration can achieve a repetition rate of at least 10 kHz.

Figure 5:
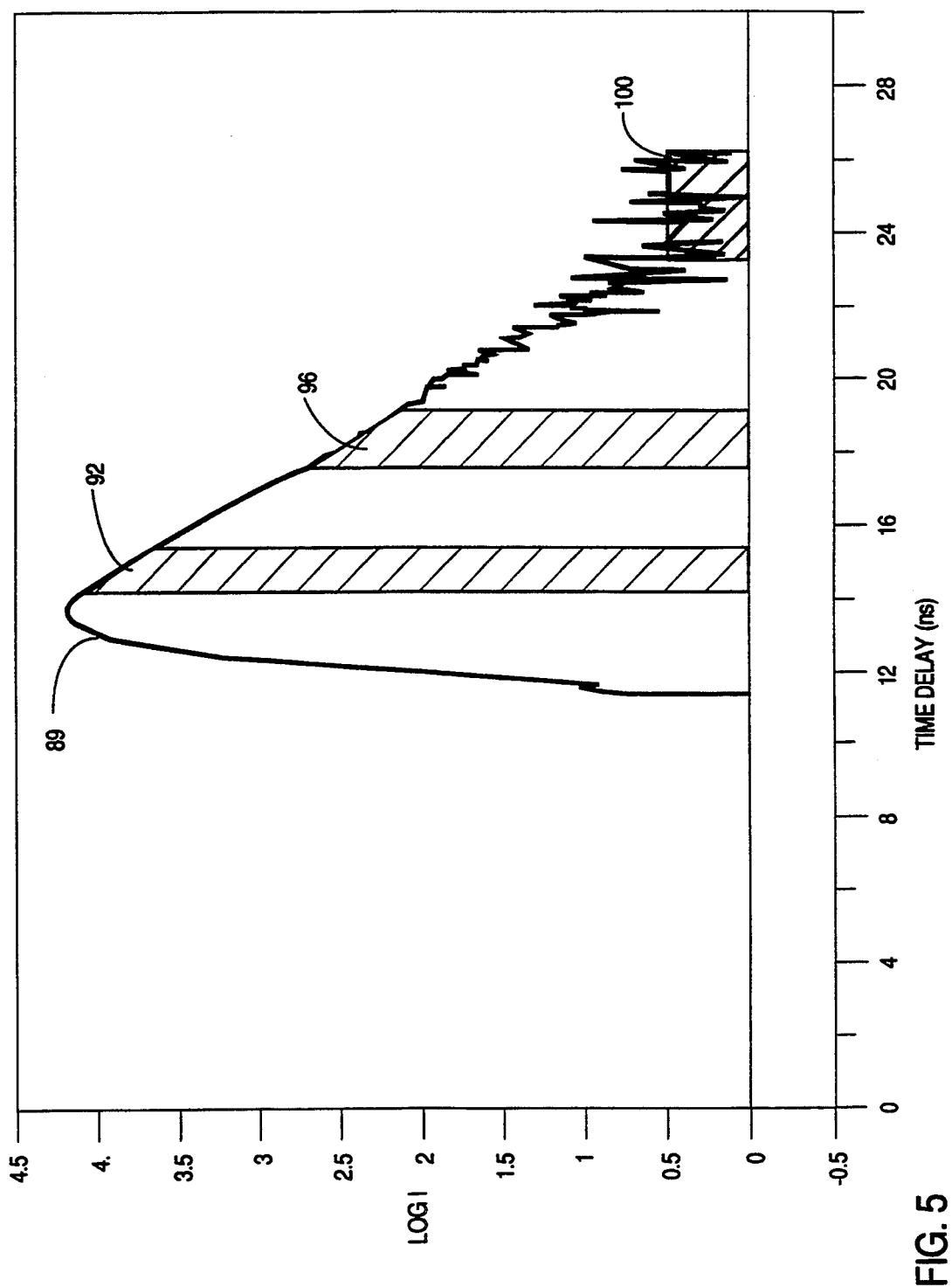
FIG. 5 and 5A show a typical time resolved spectrum and a timing diagram for the system of FIG. 4, respectively.
Figure 5A:
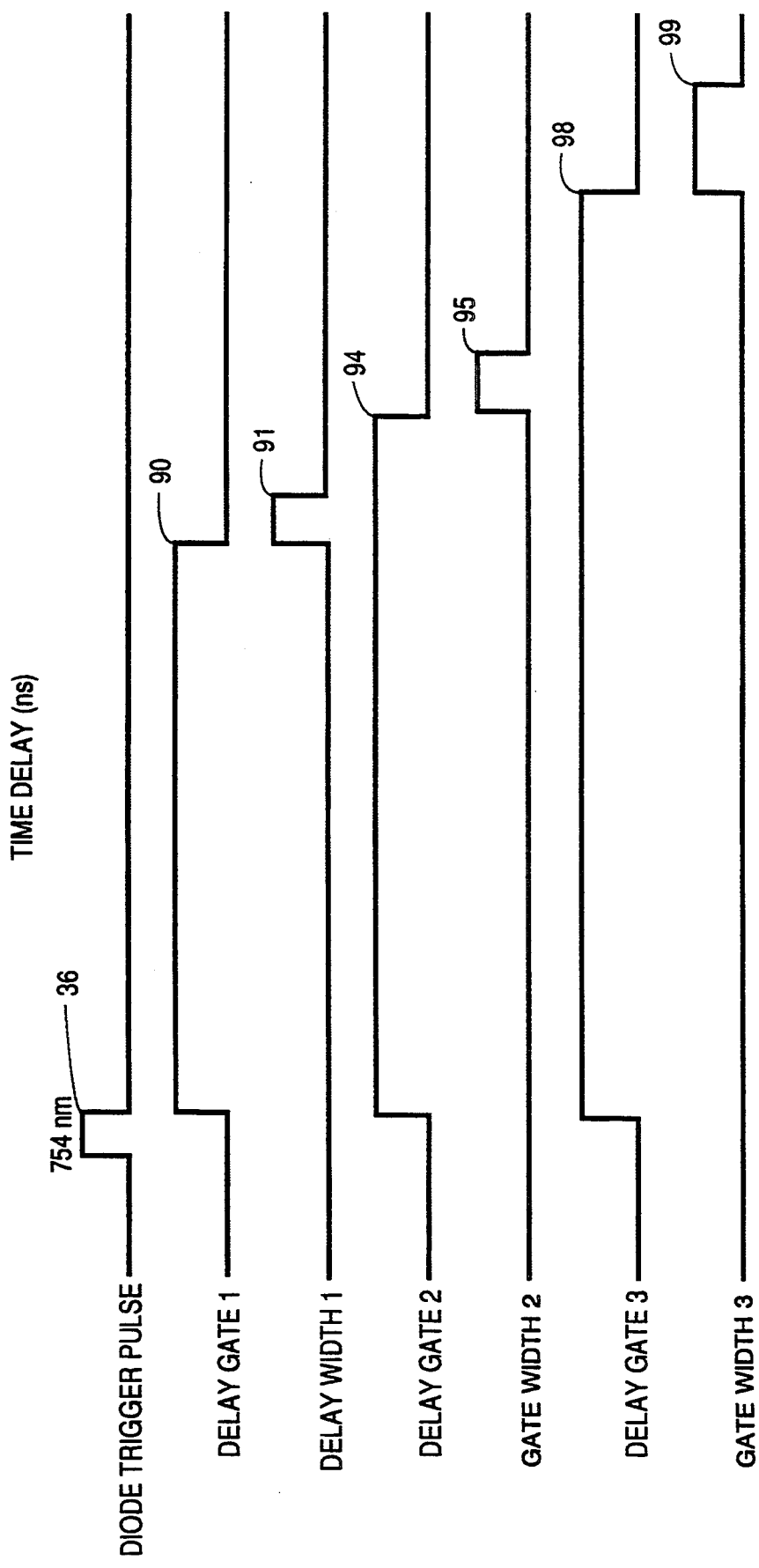

The gate arrangement of FIGS. 5 and 5A uses gates 91 and 95 to detect the decay slope of the signal while the third gate 99 may be used to determine the background signal. Outputs 92 and 96 of integrators 80 and 82 are used to calculate the slope.

To obtain approximately equal signal-to-noise ratios in the individual integrators, the length of the time windows is tailored to an exponential decay of the signal intensity with a logarithmic increase in the gate width with delay time.

Referring to FIGS. 5 and 5A, by scanning the delay gates (90, 94, and 98) and appropriately adjusting the gate widths, the system collects data corresponding to the entire detected pulse; subsequently, the shape (89) of the detected pulse is then calculated, i.e., time dependent light intensity profile I(t) is determined. The detected pulse shape, I(t), possesses information about the scattering and absorption properties of the examined tissue, which are closely related to the distribution of photon pathlengths in the tissue. The optical field is a function of the input-output port separation ($\rho$) as well as the optical properties of the tissue (absorption coefficient, $\mu_a$, scattering coefficient, $\mu_s$, and the mean cosine of anisotropic scattering, g). The general diffusion equation is used to describe the photon migration in tissue, as described by E. M. Sevick, B. Chance, J. Leigh, S. Nioka, and M. Maris in Analytical Biochemistry 195, 330 (1991) which is incorporated by reference as if fully set forth herein.

The system utilizes a previously determined solution for the fluence distribution in an infinite media as a Green's function with near infinite boundary conditions, wherein the diffusion equation is solved for the intensity of detected light in the reflectance geometry, $R(\rho,t)$, or the transmittance geometry $T(\rho,d,t)$. In the reflectance arrangement in a semi-infinite media with the separation of the input and output ports on the order of centimeters the reflectance was determined as follows:

$$\frac{d}{dt} \log_e R(\rho, t) = \frac{-5}{2t} - \mu_a c + \frac{\rho^2}{4Dct^2} \quad (2)$$

For t→∞ the absorption coefficient $\mu_a$ is determined as follows:

$$\lim_{t \to \infty} \frac{d}{dt} \log_e R(\rho, t) = -\mu_a c \quad (3)$$

wherein $\rho$ is the separation between input and detection ports and c is speed of light in the medium.

In cases where the approximation of infinite time is not valid, Eq. 2 can be rewritten to obtain $\mu_a$ as follows:

$$\mu_a c = -\frac{d}{dt} \log_e R(\rho, t) + \frac{\rho^2}{4Dct} - \frac{5}{2t} \quad (4)$$

The value for D can either be an average value for tissue or a value specific to tissue type being measured such as head or breast.

The effective scattering coefficient $(1-g)\,\mu_s$ is determined as follows:

$$(1-g)\mu_s = \frac{1}{\rho^2}(4\mu_a c^2 t_{max}^2 + 10 c t_{max}) - \mu_a \quad (5)$$

wherein $t_{max}$ is the delay time at which the detected reflectance time profile $(R(\rho,t) \equiv I(t))$ reaches maximum. The right hand side of Eq. 3 is the decay slope of the arrival time of the modified pulses.

The systems of FIGS. 1, 3, and 4 enable direct, real-time output of the absorption coefficient $\mu_a$, tissue saturation (Y), average optical pathlength ($<L>$), and the scattering coefficient $\mu_s$. The absorption coefficient is quantified by evaluating the decaying slope of the detected pulse, as described in Eq. 3. The effective scattering coefficient, $(1-g)\cdot\mu_s$, is determined from Eq. 5.

Figure 5B:
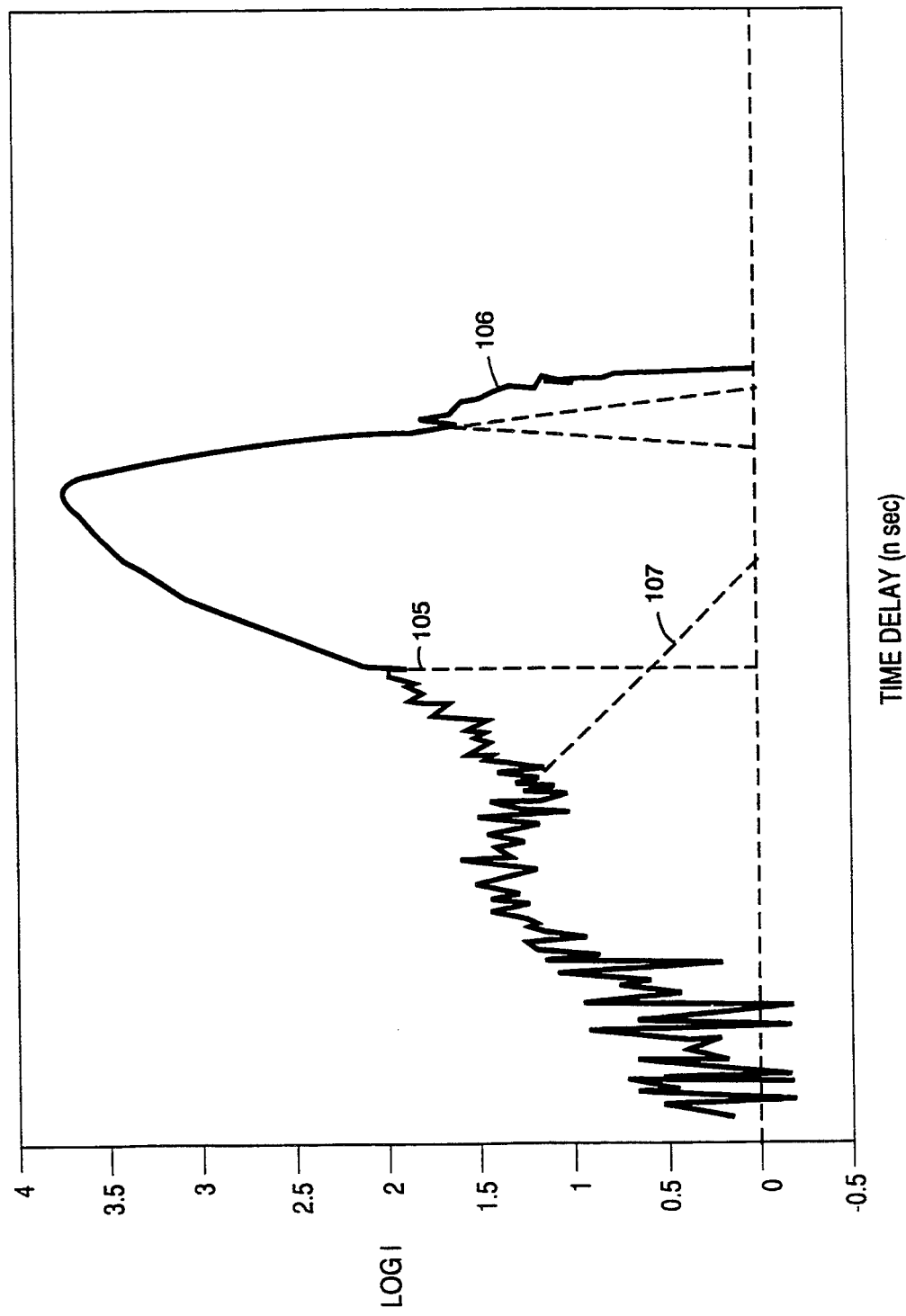
FIG. 5B shows a time resolved spectrum of photons that migrated through tissue with regions of different absorption and scattering properties.

As stated above, the intensity profile of the detected pulse, I(t), is strongly dependent on the absorption and scattering properties of the examined tissue. For a relatively homogeneous tissue (e.g., breast tissue), the detected pulse, in general, exhibits a single exponential decay (FIG. 5A). In cases wherein the light pulse migrates through different types of tissues (e.g., brain tissue that includes the white matter and the gray matter), the detected profile (I(t)) includes "two or more superimposed pulses", each characteristic of one type of tissue (Note pulse shapes 105, 106, and 107 in FIG. 5B). The TRS system of FIGS. 1, 2 or 3 scans the delay gates over the entire arrival time delay of the migrating photons to collect and deconvolute the intensity profile, I(t). A computer processor then fits iteratively the intensity profile to two or more overlapping curves and determines the scattering and absorption coefficients for each tissue effectively using Eqs. (3) and (5).

Photons introduced at the detection port are scattered on their migration path that depends on the number of scattering events. In highly scattering tissue, the time-of-flight of photons is the longest and photons have the greatest probability of penetrating larger volumes of tissue. The time-of-flight (or mean time $<t>$) is proportional to the pathlengths travelled by the photons, assuming that they travel at a speed c/n (wherein c is the speed of light in vacuum and $n \approx 1.36$ is the average refractive index of tissue). From the detected and deconvoluted photon intensity profile, I(t), a mean pathlength of the distribution of pathlengths is determined as follows:

$$<L> = \frac{c}{n} \frac{\int_0^\infty I(t) t \partial t}{\int_0^\infty I(t) \partial t} \quad (6)$$

Photon migration theory predicts that the detected photons can be represented by a three dimensional "banana-shaped" distribution pattern in the reflection geometry or a "cigar-shaped" distribution pattern in the transmission geometry. The concavity or shallow boundary is due to the escape of photons that reach the air-scatterer interface while the deeper boundary is due to attenuation of long path photons by the absorbers. If the tissue absorption properties are nonuniform, for example, when an absorbing object such as bleeding or a tumor is present, then the distribution of pathlength is also nonuniform.

The optical field is moved through tissue by increasing $\rho$ to achieve deeper field penetration or by moving the input port and the detection port in a scanning motion.

When the absorbing object is infinitely far away from the field, it does not alter the banana-shaped optical field. As the optical field is moved closer to the strongly absorbing object, the photons which have migrated the farthest distance from the input and detection ports are eliminated by the absorption process inside the absorber. Since photons with the longest pathlengths are absorbed, the approach of the field to the absorbing object shortens the distribution of pathlengths, detected as reduction in the average pathlength $<L>$. As the optical field moves even closer to the absorbing object, some of the detected photons can migrate around the object without being absorbed; this is detected as lengthening of the distribution of pathlengths. Thus, the average pathlength measurement reveals location of a strongly absorbing component of a tissue (e.g., tumor or localized bleeding); this is one way how the tissue absorbing component can be imaged.

Alternately, localization of an absorbing (or transparent) tissue component can be performed by moving the input port and the detection port on the subject and then creating two dimensional maps of absorption coefficients, scattering coefficients, saturation values, etc.

In the TRS system that includes two wavelengths sensitive to hemoglobin (Hb) and oxyhemoglobin (HbO$_2$) (e.g., 754 nm and 816 nm), the hemoglobin saturation (Y) is calculated by taking the ratio of absorption coefficients and using the following equation for the oxygen saturation:

$$Y(X100\%) = \frac{38 - 18 \frac{\mu_a^{754}}{\mu_a^{816}}}{25 + 3 \frac{\mu_a^{754}}{\mu_a^{816}}} \quad (7)$$

wherein the coefficients are determined from the extinction values of hemoglobin at 754 nm and 816 nm that are $\epsilon_{Hb} = 0.38$ cm$^{-1}$ mM$^{-1}$, $\epsilon_{Hb} = 0.18$ cm$^{-1}$ mM$^{-1}$, respectively, and the difference extinction coefficients between oxyhemoglobin and hemoglobin that are $\Delta\epsilon_{HbO-Hb} = 0.025$ cm$^{-1}$ mM$^{-1}$ and $\Delta\epsilon_{HbO-Hb} = 0.03$ cm$^{-1}$ mM$^{-1}$, respectively.

A single wavelength system of FIGS. 1, 3, and 4 can be employed for determination of the optical pathlength of photons migrating in tissue for use with CW oximeters. The pathlength is used in conjunction with the attenuation data (I/I$_O$) from the oximeters to quantitatively calculate the concentration of oxyhemoglobin using Eq. 1.

To account for difference between the geometric distance ($\rho$) of the input port and the detection port and the pathlength ($<L>$), some oximeters use a modified Beer-Lambert equation with a differential pathlength factor (DPF) as follows:

$$absorbance = DPF \cdot \epsilon \cdot [C] \qquad (8)$$

wherein [C] is the concentration of an absorbent constituent. The differential pathlength factor can not be precisely determined by the CW oximeters since it depends on the pathlength, but it can be determined using the absorption ($\mu_a$) and scattering ($\mu_s$) coefficients as follows:

$$DPF = \frac{\sqrt{3}}{2} \sqrt{\frac{(1-g)\mu_s}{\mu_a}} \qquad (9)$$

Thus a TRS system can be used to calibrate a CW oximeter to quantify the measured data.

In the studies of the brain, the TRS-pulse system is used to obtain the scattering ($\mu_a$) and absorption ($\mu_s$) coefficients at each wavelength on the white and grey matter. The absorption factors are used to determine oxygen saturation which is then used to detect hypoxia, localized bleeding and other reversible or irreversible disorders. The scattering changes in the examined tissue could be a manifestation of perinventrical hyperintense syndrome (PVH), Alzheimer's disease manifested as plaques and tangles embedded in the grey matter and others.

As implied in the earlier description, it is desirable to precisely determine the delay time of the detected pulse. In systems of FIGS. 1, 3, and 5, the pulser sends directly a trigger signal to each boxcar integrator. In the single photon counting TRS-pulse system, described in the above-cited patent application, the pulser sends a trigger signal to the time-to-amplitude converter when a pulse is emitted from the laser. However, when it is desireable to verify the time delay of the detected pulse, a third, reference fiber of known length, connected to the PMT detector, is positioned next to the input port. The detected reference pulse has a delay proportional to the length of reference fiber, and thus the time delay can be calibrated.

Figure 6:
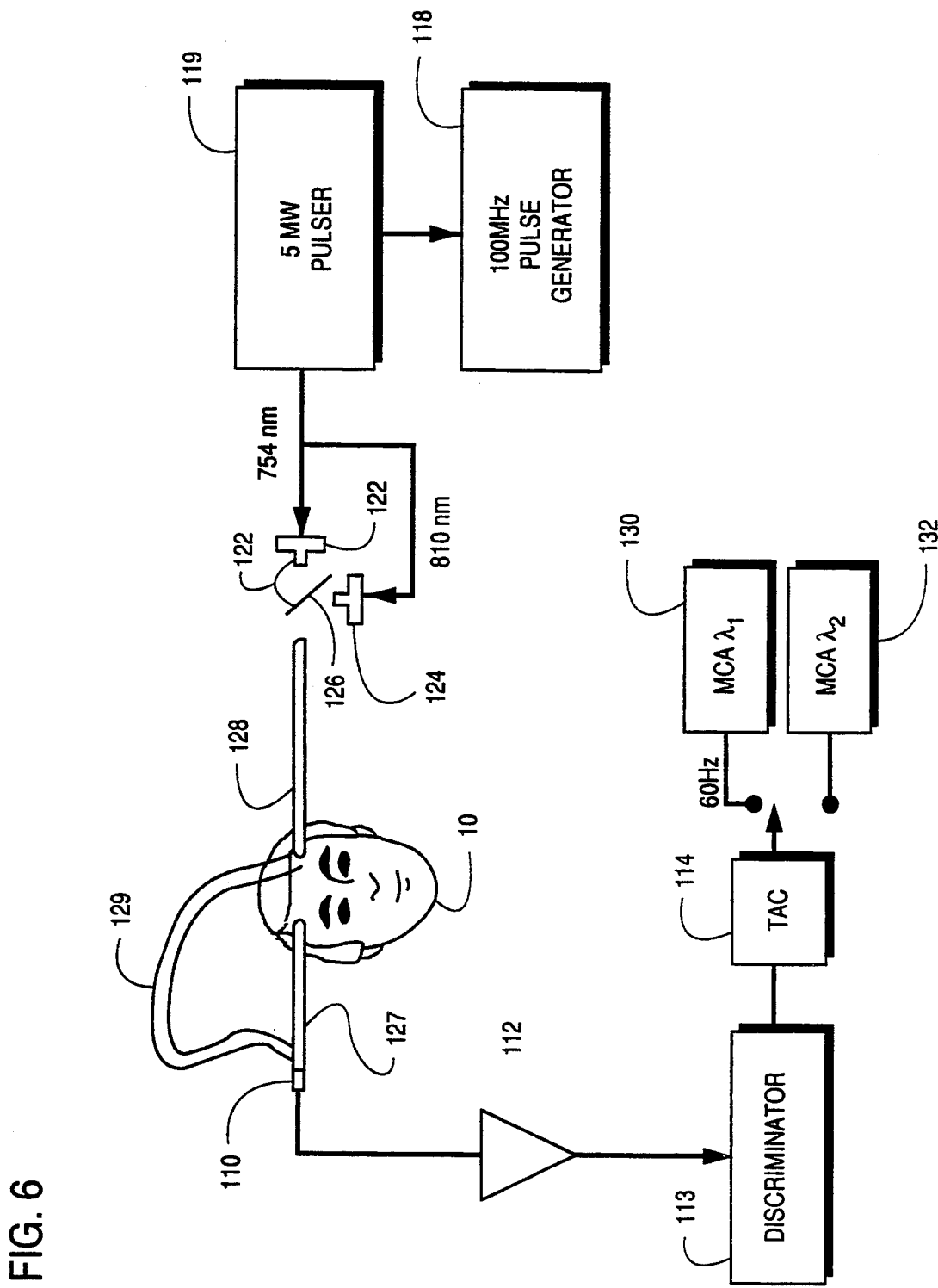
FIG. 6 is a block diagram of a TRS-pulse system utilizing an additional reference fiber adapted for time calibration.

FIG. 6 shows a block diagram of the dual wavelength TRS-pulse system adapted to reference the timing of the input pulse. Laser diodes 122, 124 (e.g., Hamamatsu PLP 10 laser diode) are driven by a 100 MHz pulse generator 118 connected to a 5 mW pulser 119. The light from lasers 122, 124 is time shared electromechanically by a 60 Hz vibrating mirror 126 so that they alternately illuminate a fiber coupler 128 that conducts pulses of light into subject 10. Photons migrate through the subject 10 to a detection port of a fiber 127 and to the detector 110 that is a photomultiplier. Additionally, a reference fiber 129 of known length is located at the input port of fiber 128 and is also connected to detector 110.

Figure 6A:
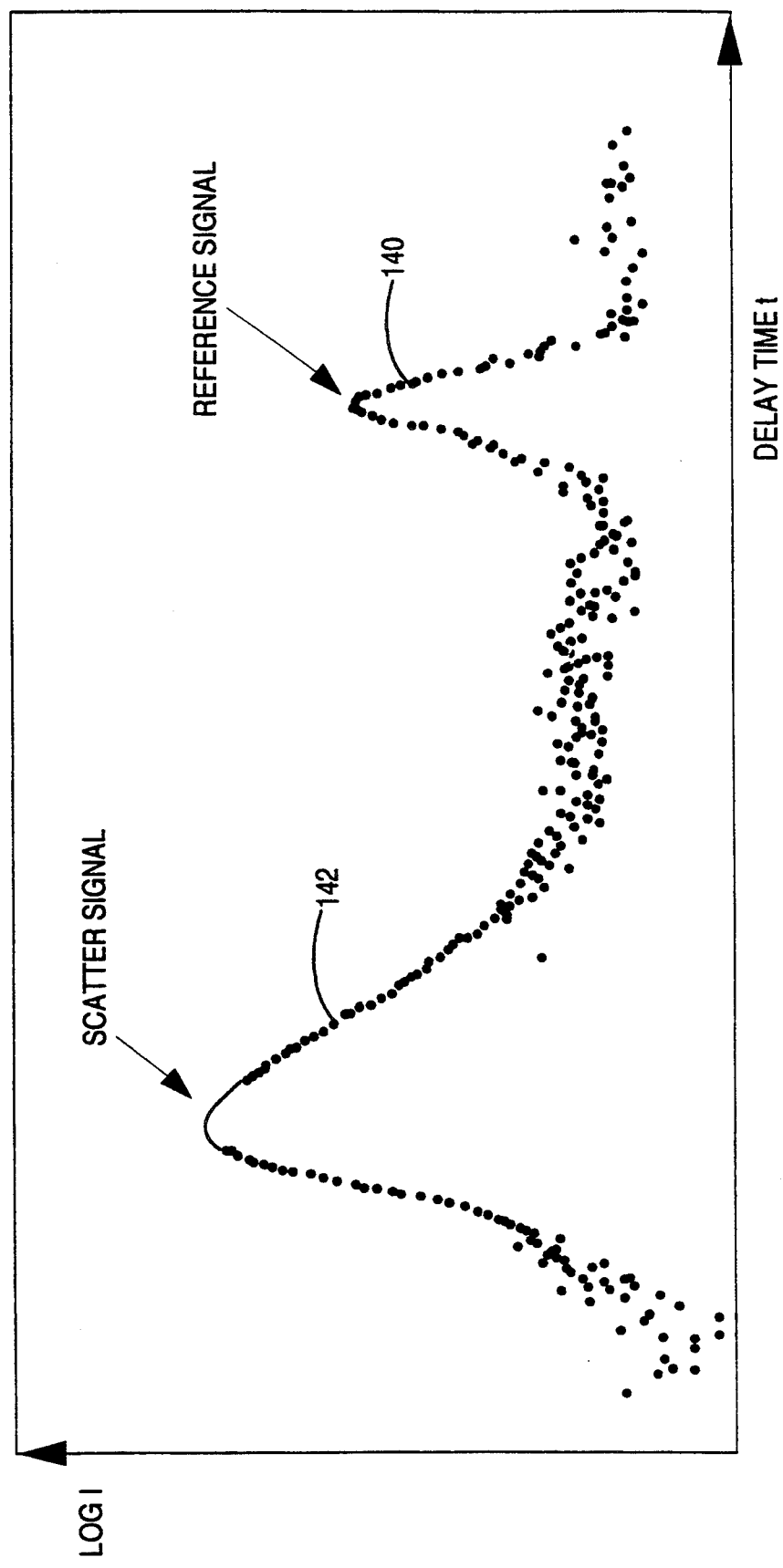
FIG. 6A is a time resolved spectrum that includes a modified pulse and a reference pulse.

The output of photomultiplier tube 110 is directly connected to a wide band amplifier 112 with appropriate roll-off to give good pulse shape and optimal signal to noise ratio. A high/low level discriminator 113 receives an output signal from amplifier 112. Discriminator 113 is a pulse amplitude discriminator wherein the threshold for acceptance of a pulse is a constant fraction of the peak amplitude of the pulse. Next, the discriminator pulses are sent to a time-to-amplitude convertor (TAC) 114. The time-to-amplitude convertor produces an output pulse with amplitude proportional to the time difference between start and stop pulses. The pulse—photon detection cycle is repeated at frequency on the order of 10 MHz to acquire a typical photon distribution. The multichannel analyzer collects only a single photon for each input light pulse. Signal from each detected photon is encoded for time delay and recorded. Following the time to amplitude conversion, the counts corresponding to the two wavelengths are separately summed in two multichannel analyzers (MCA) 130, 132, respectively. As shown in FIG. 6A, each multichannel analyzer collects and stores the time resolved spectrum that consists of detected pulse (142) modified by the examined tissue and reference pulse (140) collected by reference fiber 129 (FIG. 6). Since reference fiber 129 is located at the input port of fiber 128, the delay of the reference pulse is proportional to the known length of reference fiber 129. By comparing the known delay time of the reference pulse with the detected delay time of the reference pulse (140), the time scale of the scattered pulse (142) can be precisely calibrated.

Further embodiments are within the scope of the following claims:

We claim:

1. A method of examination of biological tissue of a subject, the scattering and absorptive properties of the examined tissue being determined by photons migrating between an optical input port and an optical detection port, said method comprising the steps of:

introducing into the tissue, at the input port, pulses of electromagnetic radiation of a selected wavelength in the visible or infra-red range, said pulses having duration on the order of a nanosecond or less;

detecting, at the detection port, photons of modified pulses that have migrated in the tissue from the input port;

integrating said photons over at least two selected time intervals separately spaced over the arrival time of said modified pulses; and determining a physiological property of the examined tissue based on the number of photons integrated over each time interval.

2. The method of claim 1 wherein the step of determining the physiological property comprises the step of determining the absorption coefficient ($\mu_a$) of the examined tissue as a function of the number of photons integrated over at least two selected time intervals separately spaced over the arrival time of said modified pulses.

3. The method of claim 2, for use under conditions in which the modified pulses have a decay slope characteristic of a property of tissue through which said photons have migrated, wherein the step of determining the absorption coefficient comprises determining said coefficient as a function of the decay slope.

4. The method of claim 2, for use under conditions in which the modified pulses have a decay slope characteristic of a property of tissue through which said photons have migrated, wherein said step of determining the absorption coefficient comprises implementing the formula:

$$\mu_a c = -\frac{d}{dt} \log_e R(\rho, t) + \frac{\rho^2}{4Dct} - \frac{5}{2t}$$

wherein $d[\log_e R(\rho,t)]/dt$ is determined from the decay slope of the arrival time of said modified pulses, D is diffusion coefficient for the examined tissue, c is speed of the light in the tissue, $\rho$ is the distance between said input and detection ports, and t is the arrival time at which the absorption coefficient is determined.

5. The method of claim 2 further comprising the step of determining a delay time ($t_{max}$) between the time a pulse is introduced into the tissue and the time the intensity of the detected corresponding modified pulse has a maximum value.

6. The method of claim 5 further comprising the step of determining the effective scattering coefficient (1-g)·$\mu_s$ of the examined tissue using the formula:

$$(1 - g)\mu_s = \frac{1}{\rho^2}(4\mu_a c^2 t_{max}^2 + 10ct_{max}) - \mu_a$$

wherein $\rho$ is a distance between said input and detection ports and c is speed of light in the tissue.

7. The method of claim 1 further comprising the steps of introducing into the tissue, at said input port, pulses of electromagnetic radiation of a second selected wavelength in the visible or infra-red range;

detecting, at said detection port, photons of modified pulses of said second wavelength that have migrated in the tissue from said input port;

integrating said detected photons over at least two selected time intervals separately spaced over the arrival time of said modified pulses; and determining a physiological property of the examined tissue based on the number of photons integrated over each time interval for each selected wavelength.

8. The method of claim 7 wherein said physiological property is absorption coefficient ($\mu_a$) at each selected wavelength and said step of determining is performed by said processor based on the number of photons integrated over at least two selected time intervals separately spaced over the arrival time of said modified pulses.

9. The method of claim 8 further comprising the step of determining concentration of a tissue pigment based on said absorption coefficients at each selected wavelength.

10. The method of claim 8 further comprising the step of determining the oxygen saturation Y based on the ratio of said absorption coefficients at each selected wavelength.

11. The method of claim 1 wherein said integrating step is performed to collect detected photons over several selected time intervals separately spaced over the entire arrival time of said modified pulses; and further comprising the step of determining intensity profile of said modified pulses over the entire arrival time.

12. The method of claim 11 further comprising the step of determining a mean pathlength of the distribution of the photon migration pathlengths.

13. The method of claim 12 further comprising the step of calibrating data measured by a continuous wave oximeter using said mean pathlength.

14. The method of claim 1 wherein said step of introducing pulses, comprises introducing pulses of a selected wavelength in the range of 600 nm to 1000 nm.

15. The method of claim 1 wherein the step of introducing pulses, comprises introducing pulses of a selected wavelength in the near infrared range.

16. A system for examination of biological tissue of a subject, the scattering and absorptive properties of the examined tissue being determined by photons migrating between an optical input port and an optical detection port, said system comprising:

an optical input port located at a first location to introduce light to the biological tissue;

an optical detection port located at a second location spaced apart from said input port to detect light that has migrated through the biological tissue;

the source means for introducing into the tissue, at the input port, pulses of electromagnetic radiation of a selected wavelength in the visible or infra-red range, said pulses having duration on the order of a nanosecond or less;

detector means for detecting, at the detection port, photons of modified pulses that have migrated in the tissue from the input port;

integrator means, coupled to said detector means, for integrating said photons over at least two selected time intervals separately spaced over the arrival time of said modified pulses; and processor means, coupled to said integrator means, for determining a physiological property of the examined tissue based on the number of photons integrated over each time interval.

17. The system of claim 16 wherein said processor means further determines an absorption coefficient ($\mu_a$) of the examined tissue based on the number of photons integrated over at least two selected time intervals separately spaced over the arrival time of said modified pulses.

18. The system of claim 17 wherein said processor means calculates the absorption coefficient ($\mu_s$) as a function of a decay slope of said modified pulses, said decay slope of said modified pulses being characteristic of a property of tissue through which said photons have migrated.

19. The system of claim 17 wherein said processor means calculate the absorption coefficient ($\mu_a$) using the formula:

$$\mu_a c = -\frac{d}{dt}\log_e R(\rho, t) + \frac{\rho^2}{4Dct} - \frac{5}{2t}$$

wherein $d[\log_e R(\rho,t)]/dt$ is determined from a decay slope of the arrival time of said modified pulses, said decay slope of said modified pulses being characteristic of a property of tissue through which said photons have migrated; D is diffusion coefficient for the examined tissue, c is speed of the light in the tissue, $\rho$ is the distance between said input port and said detection port; and t is the arrival time at which the absorption coefficient is calculated.

20. The system of claim 17 wherein said processor means further determines a delay time ($t_{max}$) between the time a pulse is introduced into the tissue and the time the intensity of the detected corresponding modified pulse has a maximum value.

21. The system of claim 20 wherein said processor means further determines the effective scattering coefficient (1-g)·$\mu_s$ of the examined tissue using the formula:

$$(1 - g)\mu_s = \frac{1}{\rho^2}(4\mu_a c^2 t_{max}^2 + 10ct_{max}) - \mu_a$$

wherein $\rho$ is a distance between said input and detection ports and c is speed of light in the tissue.

22. The system of claim 16 wherein said source means further introduces into the tissue, at said input port, pulses of electromagnetic radiation of a second selected wavelength in the visible or infra-red range;

said detector means detects, at said detection port, photons of modified pulses of said second wavelength that have migrated in the tissue from said input port;

said integrator means integrates said detected photons over at least two selected time intervals separately spaced over the arrival time of said modified pulses of said second wavelength; and said processor means determines a physiological property of the examined tissue based on the number of photons integrated over each time interval for each selected wavelength.

23. The system of claim 22 wherein said processor means further determines an absorption coefficient ($\mu_a$) of the examined tissue, at each selected wavelength, based on the number of photons integrated over at least two selected time intervals separately spaced over the arrival time of said modified pulses of said wavelengths.

24. The system of claim 23 wherein said processor means further calculates concentration or a tissue pigment based on said absorption coefficients at each selected wavelength.

25. The system of claim 23 wherein said processor means further calculates the oxygen saturation Y based on the ratio of said absorption coefficients at each selected wavelength.

26. The system of claim 16 wherein said integrator means further collects detected photons over several selected time intervals separately spaced over the entire arrival time of said modified pulses; and said processor means determines intensity profile of said modified pulses over the entire arrival time.

27. The system of claim 26 wherein said processor means calculates a mean pathlength of the distribution of the photon migration pathlengths.

28. The system of claim 27 further comprising a continuous wave oximeter, connected to said processor means, receiving a value of said mean pathlength for calibrating its values of tissue oxygenation.

29. The system of claim 16 wherein said source means introduces said pulses of said selected wavelength in the range of 600 nm to 1000 nm.

30. The system of claim 16 wherein said source means introduces said pulses of said selected wavelength in the near infrared range.

* * * * *

UNITED STATES PATENT AND TRADEMARK OFFICE
CERTIFICATE OF CORRECTION

PATENT NO.  : 5,386,827

DATED       : February 7, 1995

INVENTOR(S) : Britton Chance and Kenneth J. Kaufmann

It is certified that error appears in the above-identified patent and that said Letters Patent is hereby corrected as shown below:

On the cover page

Item [73], add the second assignee --Photonics Research Corporation, Bridgewater, NJ--.

Column 3, line 10; insert --has-- after "pulse".

Column 4, line 61; insert --approximately-- after "from".

Column 11, line 38; "pulses" should be --pulse--.

Signed and Sealed this

Nineteenth Day of March, 1996

Attest:

BRUCE LEHMAN

Attesting Officer     Commissioner of Patents and Trademarks